United States Patent
Stensrud et al.

(10) Patent No.: US 10,155,736 B2
(45) Date of Patent: Dec. 18, 2018

(54) ESTERIFICATION OF 2,5-FURAN-DICARBOXYLIC ACID

(71) Applicant: Archer Daniels Midland Company, Decatur, IL (US)

(72) Inventors: Kenneth Stensrud, Decatur, IL (US); Padmesh Venkitasubramanian, Forsyth, IL (US)

(73) Assignee: Archer Daniels Midland Company, Decatur, IL (US)

( * ) Notice: Subject to any disclaimer, the term of this patent is extended or adjusted under 35 U.S.C. 154(b) by 0 days.

(21) Appl. No.: 15/674,726

(22) Filed: Aug. 11, 2017

(65) Prior Publication Data

US 2017/0369463 A1    Dec. 28, 2017

Related U.S. Application Data

(62) Division of application No. 14/650,586, filed as application No. PCT/US2013/073821 on Dec. 9, 2013, now Pat. No. 9,765,045.

(60) Provisional application No. 61/739,761, filed on Dec. 20, 2012.

(51) Int. Cl.
*C07D 307/68* (2006.01)
*C12P 17/04* (2006.01)

(52) U.S. Cl.
CPC .......... *C07D 307/68* (2013.01); *C12P 17/04* (2013.01); *Y02P 20/544* (2015.11); *Y02P 20/582* (2015.11)

(58) Field of Classification Search
CPC ..... Y02P 20/544; Y02P 20/582; C07D 307/68
See application file for complete search history.

(56) References Cited

PUBLICATIONS

Fischer. Arkivoc, 2013, (iv), 405-412 (Year: 2013).*

* cited by examiner

*Primary Examiner* — Noble E Jarrell
(74) *Attorney, Agent, or Firm* — William B. Miller

(57) ABSTRACT

A method of making a furan dicarboxylate by means of reacting 2,5-furan dicarboxylic acid (FDCA) with an alcohol or mixture of alcohols in a $CO_2$-predominant atmosphere without the presence of any other acid catalyst is described. The reaction is conducted under conditions that correspond to either supercritical, critical or near-critical temperatures and pressures for the alcohol species and/or $CO_2$ gas.

13 Claims, 3 Drawing Sheets

ESTERIFICATION OF 2,5-FURAN-DICARBOXYLIC ACID

PRIORITY CLAIM

The present Application is a divisional of U.S. patent application Ser. No. 14/650,586 filed 9 Jun. 2015 which is a 371 National Phase Entry of International Patent Application No. PCT/US13/73821 filed 9 Dec. 2013 which claims benefit of priority from U.S. Provisional Application No. 61/739,761, filed Dec. 20, 2012, the contents of which are incorporated herein.

FIELD OF INVENTION

The present invention relates to an esterification process. In particular, the invention pertains to the conversion of furan dicarboxylic acid to esters with an alcohol and $CO_2$.

BACKGROUND

Biomass contains carbohydrates or sugars (i.e., hexoses and pentoses) that can be converted into value added products. Production of biomass-derived products for non-food uses is a growing industry. Bio-based fuels are an example of an application with growing interest. Another application of interest is the use of biomass as feedstock for synthesis of various industrial chemicals from renewable hydrocarbon sources.

In recent years, an increasing effort has been devoted to find ways to utilize biomass as feedstock for the production of organic chemicals because of its abundance, renewability, and worldwide distribution. When considering possible downstream chemical processing technologies, the conversion of sugars to value-added chemicals is very important. Recently, the production of furan derivatives from sugars has become exciting in chemistry and in catalysis studies, because it aids one of the major routes for achieving sustainable energy supply and chemicals production. As illustrated in FIG. 1, which shows a schematic representation of a process for converting biomass into useful end products, furanic intermediates: 5-hydroxymethylfurfural (5-HMF), 2,5-furan-dicarboxylic acid (2,5-FDCA) and 2,5-dimethylfuran (2,5-DMF) have been called the "sleeping giants" of renewable intermediate chemicals. These intermediates are green building blocks for a range of materials, chemicals and fuels. As building blocks that have been much studied, and have enormous potential for use in the production of green plastics and chemicals, the U.S. Department of Energy has recognized furanic intermediates as one of the top high-potential green building blocks. 5-HMF is a dehydration product of hexoses and a potential substitute of petroleum-based building blocks of various polymers. 2,5-FDCA is derived from oxidative dehydration of hexoses and is considered as one of the top 12 compounds made from a sugar into a value-added chemical. 2,5-DMF is produced through hydrogenation of HMF and is less volatile and of 40% higher energy density than ethanol. (See generally, T. Werpy, G. Petersen, TOP VALUE ADDED CHEMICALS FROM BIO-MASS: Vol. I—Results of Screening for Potential Candidates from Sugars and Synthesis Gas, August 2004. (Available electronically at http://www.osti.gov/bridge))

Even though much interest has arisen to develop better ways of making building blocks for the emerging market of green materials and renewable energy, until recently, furanics have not been commercialized because large-scale production of furanic intermediates have not been cost-effective. Various different processes have been advanced for the catalytic conversion of sugar to furan chemicals. (See generally, X. Tong et al., "Biomass into Chemicals: Conversion of Sugars to Furan Derivatives by Catalytic Processes," APPLIED CATALYSIS A: GENERAL 385 (2010) 1-13.)

Of the furanic intermediates, furan-dicarboxylic acid (FDCA) is a commercially valuable material that can used as a precursor for various plasticizers, or a replacement for purified terephthalic acid (PTA), or other value added products. Over the years, chemical manufacturers have sought a simpler way of producing and manipulating FDCA, given the known problems associated with working with FDCA, such as its poor solubility in common organic solvents and being soluble in high boiling solvents like DMSO. Another problem that arises when using FDCA in melt polymerization is the tendency for the FDCA molecule to decompose at temperatures greater than about 180° C. to furoic acid, leading to poor product quality. All of these challenges can be solved by derivatizing FDCA into an ester. Current acid catalyzed esterification, however, typically requires about 20 hours or more to produce diester molecules. Such a process takes too long and is not cost effective for high-volume, mass production of the esters. Furthermore, purification of the resulting esters requires washing with base to remove residual acid catalyst that may affect the quality of the FDCA esters in downstream processing. Other alternatives for esterification of FDCA require its activation as a diacyl chloride, which makes the process not sustainable or economical.

The preparation of an acyl chloride (i.e., COCl moiety) requires treating an acid with thionyl chloride in stoichiometric amount and then converting it to an ester. Safety concerns arise when using thionyl chloride on a large scale, as the byproducts for the acylation reaction are $SO_2$ and HCl, and HCl for the esterification. The $SO_2$ and HCl are captured with a weak base and then disposed as waste. Moreover, conversion of FDCA to the corresponding furan-2,5-dicarbonyl dichloride would generate a mixture of side products upon esterification with alcohols because of unstable intermediates. Additionally, the acyl chloride is sensitive to water and would require special storage conditions.

WO 2011/023590 A1 by Grass et al. describes, in part, methods for producing mixtures of ester derivatives of 2,5-furan dicarboxylic acid (FDCA) and the use of the derivative material (isononyl furan dicarboxylate) as plasticizers. In particular, the disclosure relates a method using an acid or metal catalyst for preparing esters of FDCA with isomeric C-9 alcohols, in particular mixtures of linear and branched nonanols (e.g., isononyl furan-2,5-dicarboxylate). The method follows largely a conventional process of esterification. According to Grass et al., one can prepare an ester using either FDCA or a reactive derivative such as the corresponding dichloride with a strong mineral acid. Further, the method unfortunately experiences certain disadvantages, such as: FDCA at temperatures above 190° C. tends to eliminate $CO_2$, and forms monocarboxylic acids (e.g., furoic acid), which cannot be converted to the desired product, and to avoid the formation of color and decomposition of FDCA at the reaction temperatures one may need to use dimethyl furan dicarboxylate as a precursor.

In view of such issues of converting or synthesizing esters of FDCA according to current techniques, a need exists for a simple, clean, and economic process for converting carbohydrates into building blocks for materials and fuels for commercialized use.

SUMMARY OF THE INVENTION

The present invention relates to a method of producing one or more furan dicarboxylates. The method involves in a first embodiment: reacting 2,5-furan dicarboxylic acid (FDCA) with at least an alcohol or a mixture of different alcohols in a $CO_2$ atmosphere in the substantial absence of any other extrinsic catalyst, according to the following:

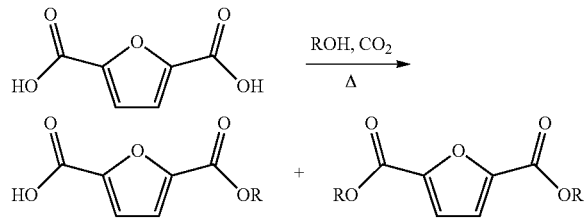

to yield a mixture of esters, wherein R-group is at least a saturated, unsaturated, cyclic, or aromatic group. The $CO_2$ functions as a self-generating acid catalyst in situ and regenerates back to a reagent during ester synthesis. The esterification reaction of FDCA with an alcohol in $CO_2$ is performed under operational conditions that correspond to either supercritical, critical or near-critical reaction temperatures or pressures for at least the alcohol species or $CO_2$. In certain embodiments, the synthesis is performed at a reaction temperature between about 150° C. and 250° C., at a reaction pressure of about 400 psi up to about 3,000 psi. The method may further entail reaction of the ester product in a second esterification reaction to regenerate the alcohol reagent, and recycling the alcohol back to react with additional FDCA.

In another aspect, the disclosure relates to a method of processing furan dicarboxylic acid (FDCA). The method involves: reacting FDCA with a first alcohol in $CO_2$ atmosphere in the substantial absence of any other catalyst to produce a first ester mixture; reacting said first ester mixture with a second alcohol in a transesterification reaction to produce a second ester mixture. One may regenerate the first alcohol and recycling the first alcohol back to react with additional FDCA. The method can be adapted for either batch or continuous processing operations.

Additional features and advantages of the present methods will be disclosed in the following detailed description. It is understood that both the foregoing summary and the following detailed description and examples are merely representative of the invention, and are intended to provide an overview for understanding the invention as claimed.

DETAILED DESCRIPTION OF THE INVENTION

Section I—Description

The present invention involves the discovery of a simple and effective way of producing esters from furan-dicarboxylic acid (FDCA). An aspect of the inventive method uses carbon dioxide ($CO_2$) as an acid catalyst in esterification reactions, without the presence of any other acid catalyst. The present method is an environmentally benign way to produce mono- and/or di-alkyl furan dicarboxylates. The method involves a liquid reaction system.

Figure 1:
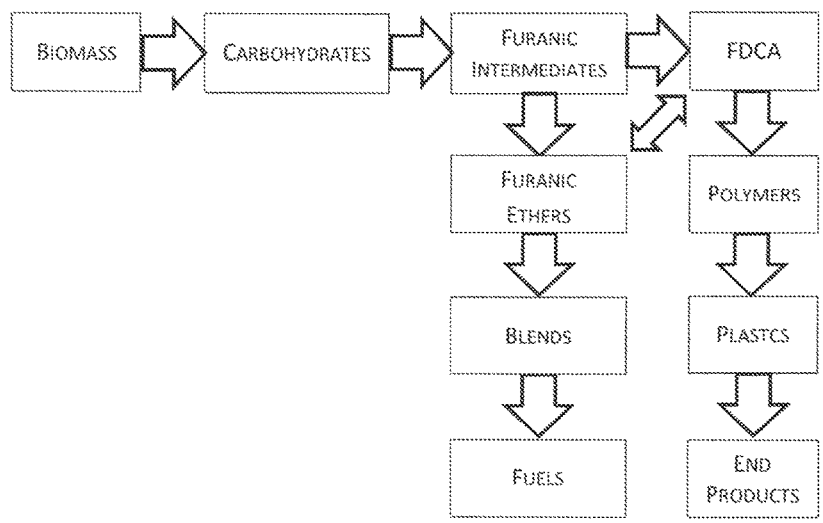
FIG. 1 is a schematic overview of the general steps involved in refining biomass into furanic intermediates that can be further processed along value chains for either polymer molecules used in materials or fuels.

The method enables one to use the resulting mono- or di-alkyl furandicarboxylates as a precursor for useful compounds for polymer materials, plasticizers, or fuels along downstream pathways such as illustrated in FIG. 1. For example, dimethyl furan dicarboxylates can be a precursor for plasticizers such as terephthalic acid or isononyl furandicarboxylate, or for various polymers, such as polyethylene furan-dicarboxylate or isosorbide FDCA esters for high glass-transition temperature ($T_g$) polymers. Monomethyl furan dicarboxylates can be a precursor for higher alcohol alkyl esters that can be used as cationic surfactants, chelators, and corrosion inhibitors. Alternatively, some mono-alkyl esters made by the present invention can be used directly as fungicides in wood preservation.

An advantageous feature of the inventive method is that activation of the free carboxylic acid as an acyl halide (e.g., fluoride, chloride, bromide) or by using strong mineral acids is unnecessary unlike with some other techniques. Acyl halides are inconvenient to use because these species are inherently reactive, have issues with stability, waste treatment, and can be cumbersome and costly to make. An acyl chloride is a more reactive species than FDCA.

Conventionally, the mechanism for the formation of an ester from an acid and an alcohol is the reverse of the steps for the acid-catalyzed hydrolysis of an ester, and the reaction can go in either direction depending on the conditions used. In a typical esterification process, a carboxylic acid does not react with an alcohol unless a strong acid is used as a catalyst. The catalyst is usually concentrated sulfuric acid or hydrogen chloride. Protonation makes the carbonyl group more electrophilic and enables it to react with the alcohol, which is a weak nucleophile.

In general terms, the present esterification process involves a reaction of FDCA with an alcohol in a $CO_2$ atmosphere in the substantial absence of any other acid catalyst to produce esters. As used herein, the term "substantial absence" refers to a condition in which an acid catalyst is either largely or completely absent, or is present in de minimis or trace amount of less than catalytic efficacy. In other words, no other acid catalyst is present, or is present at a level less than 10%, 5%, 3%, or 1% weight/weight relative to the carboxylic acid in the reaction. The esterification reaction is performed in solution under conditions that are either at supercritical, critical or near critical temperatures and/or pressures for either the alcohol and/or $CO_2$. Under such conditions, we believe that $CO_2$ self-generates or functions in situ as an acid catalyst, and regenerates in situ subsequently back into a reagent. Carbonic acid is much weaker than the usual strong acids. Nonetheless, a reactive intermediate (monoalkylcarbonic acid) is being made in situ in large enough quantities to drive esterification and effect ester production. The observed trend of greater ester conversion at higher temperatures adduces a relatively large energy of activation for this process.

Figure 2:
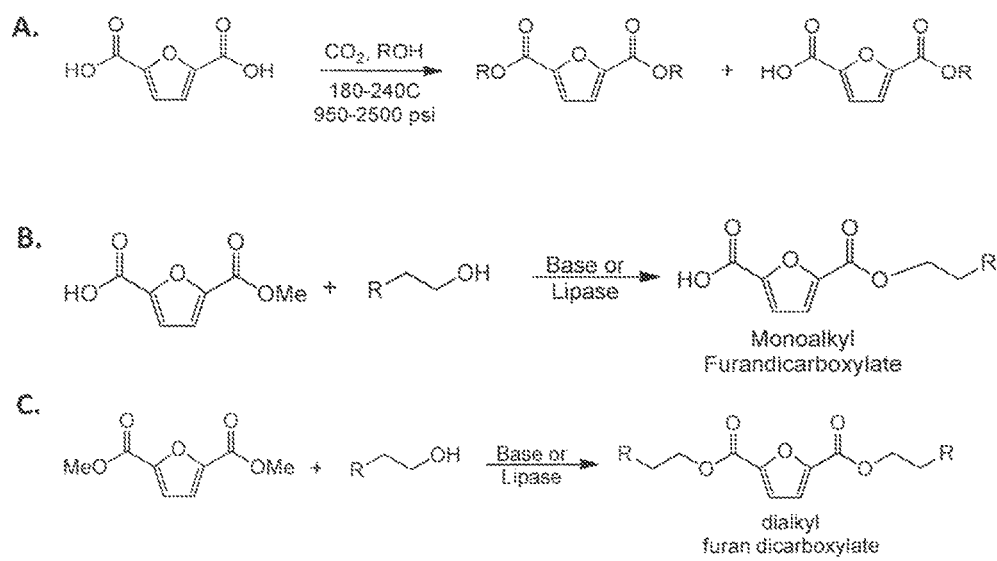
FIG. 2 is a general illustration of an esterification reaction of FDCA, and subsequent transesterification reaction of ester products according to an embodiment of the present invention.

FIG. 2A is an equation that represents certain embodiments of the present esterification method. FDCA is reacted with an alcohol (ROH) in a $CO_2$ atmosphere, at a heightened temperature, such as between 180° C. and 240° C., and pressure, such as 950 psi to 3000 psi (gauge). Typically, the resulting ester products can be either monoesters or diesters, or a mixture of both. One can control the reaction to drive the esterification toward either the monoesters or diesters, or a certain mixture of mono- and diesters. For instance, one may select a reaction temperature and pressure that preferentially drives the esterification reaction towards formation of diester molecules. One can separate the mono-alkyl esters from di-alkyl esters by means of crystallization, distillation, ion exchange resin, or acid-base extraction techniques.

FIGS. 2B and 2C, respectively, show subsequent tranesterification of the mono- and diakyl esters by means of either base-catalyzed or enzymatic reactions, such as by means of a lipase enzymatic reaction. The lipase can be derived from a variety of microbes, such as *Candida antartica*, which is available commercially under the tradename NOVOZYM™ 435.

Figure 3:
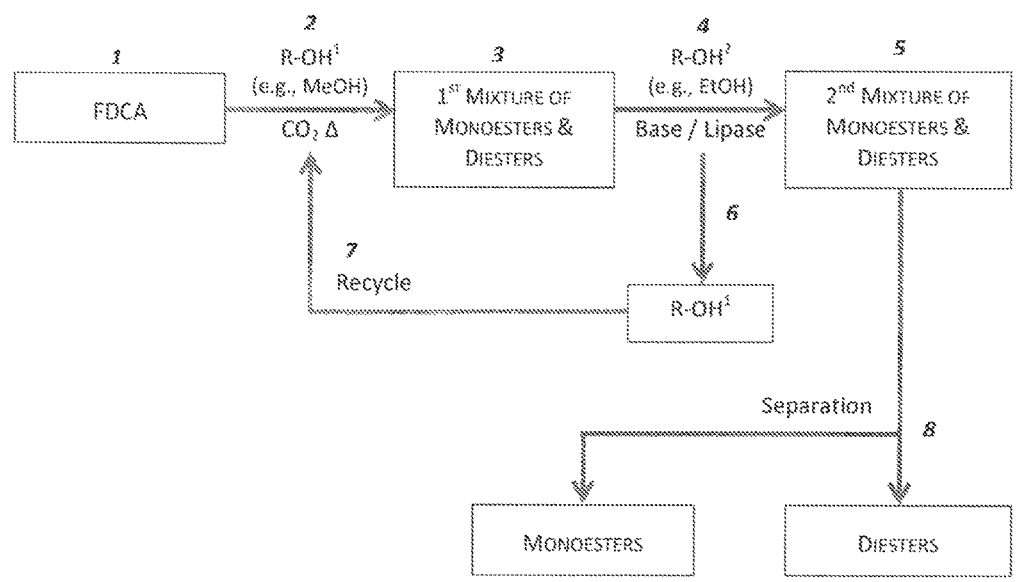
FIG. 3 is a schematic representation of a continuous esterification and recovery process according to an embodiment of the present invention.

FIG. 3 illustrates another aspect of the present invention that pertains to a method of processing FDCA. The method involves: reacting FDCA 1 with a first alcohol (R—OH') in a $CO_2$ atmosphere 2 in substantial absence of any other catalyst to produce a first ester mixture 3; reacting the first ester mixture with a second alcohol (R—$OH^2$) in a transesterification reaction 4 to produce a second ester mixture 5. The mono- and dialkyl esters produced in the reaction with the first alcohol species (e.g., methanol) are transesterified with the second alcohol species (e.g., ethanol). The first ester mixture may include either mono-esters or diesters, such as according to certain embodiments, any one of the following species: methyl furan dicarboxylate, ethyl furan dicarboxylate, propyl furan dicarboxylate, or etc.

The transesterification reaction 4 can be performed at a lower temperature than the first esterification reaction, for example, at about 80° C. to about 90° C., and a reduced pressure at the boiling point of the first alcohol species. That is, one can apply negative pressure, a partial-vacuum, to lower the pressure in the reactor. The boiling point of the second alcohol should be at least 10° C.-20° C. (e.g., 12° C., 15° C.) greater than the boiling point of the first alcohol. This will help liberate and separate the first and second alcohol species 6. The alcohol, such as methanol, released during the condensation reaction of the mono- or dialkyl esters can be recycled 7 back for synthesis of more mono- and/or dialkyl furan dicarboxyate, such as depicted in FIG. 3. This feature enables one to operate the present process either continuously or in batches. The monoesters and diesters in the second ester mixture 5 can be separated 8 from each other thereafter.

In the present esterification process, both the catalyst ($CO_2$) and the esterification reagent (alcohol) are present in large excess relative to the amount of organic acid. $CO_2$ should be in the gas phase during the reaction phase, regardless of its origin (e.g., gas tank or dry ice), as the reaction is conducted at high temperatures. Addition of solid $CO_2$ is strategic in the case where sealed pressure reactors are used, in that it allows for slow sublimation of gaseous $CO_2$ formation as the reaction apparatus is being assembled. This can minimize $CO_2$ loss. In a $CO_2$ (i.e., $CO_2$-containing) atmosphere, the concentration of $CO_2$ in the reaction atmosphere can be at least 10% or 15% by volume, favorably about 25% or 30%, preferably greater than 50%. For better reaction results, the concentration of $CO_2$ should be maximized. Desirable concentrations of $CO_2$ are from about 75% or 80% to about 99.9% by volume, typically between about 85% and about 98%. Nitrogen ($N_2$) gas or air is permissible in the reactor, but preferably the concentration of gases other than $CO_2$ is kept at either a minor percentage (<50%) or de minimis amount.

Any liquid alcohol with an R-group of $C_1$-$C_{20}$ can serve as the solvent reagent or first alcohol species. The R-group can be at least a saturated, unsaturated, cyclic, or aromatic species. A mixture of different kinds of alcohols (e.g., $C_1$-$C_{12}$) can also be used in the reaction, but will produce a corresponding mixture of different esters depending on the particular R-group. Certain lower alcohol species with $C_1$-$C_6$ alkyl groups are preferred as the reagent in the first esterification with $CO_2$ in view of their common availability, inexpensiveness, and mechanistic simplicity in the esterification reaction. Further, alcohols such as methanol, ethanol, propanol, or butanol are preferred because of parameters such as their comparatively simple structure and that the reactions are more easily controlled with respect to the supercritical, critical or near critical temperatures and pressures of these alcohol species. Alternatively, in some embodiments, the alcohol can also be a $C_2$-$C_6$-diol. Esterification with a diol can generate monomers or low molecular weight oligomers that can be readily polymerized.

When processing the ester products from the esterification with $CO_2$ in the later or second transesterification reaction, any kind of liquid alcohol species with at least a $C_2$—R-group formula may be used as the second alcohol reagent. The R-group can be at least a saturated, unsaturated, cyclic, or aromatic species. Depending on the desired ester compounds, higher alcohols species with longer carbon chains, such as $C_3$-$C_{10}$ or $C_{12}$-$C_{18}$ alkyl groups, may be preferred. Typically, however, alcohols with R-groups of $C_2$-$C_6$ or $C_8$ are more convenient and easily to use as reagents. The alcohol can also be a $C_2$-$C_6$-diol.

In general, the esterification process is conducted at a reaction temperature between about 160° C. and about 250° C., at a reaction pressure of between about 400 psi or 500 psi and 2,500 or 2,800 psi (gauge), for an extended, at least 4 hours, up to about 12 hours. Particular reaction times may vary but are usually less, such as between about 5 or 6 hours and about 8 or 10 hours. Typically, the reaction temperature can be in a range from about 170° C. or 190° C. to about 230° C. or 245° C. (e.g., 175° C., 187° C., 195° C. or 215° C.), and the reaction pressure is between about 900 psi or 950 psi and about 2,200 psi or 2,400 psi (e.g., 960 psi, 980 psi, 1020 psi or 1050 psi). Alternatively, the temperature can be in a range from about 180° C. to about 240° C. (e.g., about 185° C. or 200° C. to about 220° C. or 235° C.), and the reaction temperature is between about 1,000 psi and 2,350 psi (e.g., 1,100 psi, 1,250 psi, 1,500 psi, 1,700 psi, 1,820 psi, or 1,900 psi). Other reaction temperatures may be within a range, for example, from about 160° C. or 175° C. to about 210° C. or 225° C., and other reaction pressures may be within a range, for example, from about 1,200 psi or 1,630 psi to about 1,800 psi or 2,100 psi.

These reaction temperatures and pressures correspond to supercritical, critical or near critical conditions for the alcohol(s) or $CO_2$. Table 1 lists, for purpose of illustration, critical parameters for some common solvents (i.e., methanol, ethanol, 1-propanol, 1-butanol, water, and $CO_2$).

TABLE 1

Critical Data for Select Substances (Yaws, C. L., Chemical Properties Handbook. In McGraw-Hill: 1999; pp 1-29.)

| Substance Name | Molecular Weight | Critical Temp. (K)/° C. | Critical Pressure (bar)/psi | Critical Density (g/cm$^3$) |
|---|---|---|---|---|
| Methanol | 32.042 | 512.58/239.43 | 80.96/1174.2255 | 0.2720 |
| Ethanol | 46.069 | 516.25/243.10 | 63.84/925.9209 | 0.2760 |
| 1-Propanol | 60.095 | 537.4/264.25 | 51.02/739.9839 | 0.2754 |
| 1-Butanol | 74.122 | 563.0 ± 0.3/289.85 | 45.0 ± 4.0/652.671 | 0.3710 |
| Water | 18.015 | 647.13/373.98 | 220.55/3198.8071 | 0.3220 |
| Carbon dioxide | 44.010 | 304.19/31.04 | 73.82/1070.6685 | 0.4682 |

At conditions above the critical point (i.e., critical temperature and/or pressure), the fluid exists in a super critical phase where it exhibits properties that are in between those of a liquid and a gas. More specifically, supercritical fluids have a liquid-like density and gas-like transport properties (i.e., diffusivity and viscosity). This can be seen in Table 2, wherein the typical values of these properties are compared between the three fluid types—conventional liquids, supercritical fluids, and gases.

TABLE 2

Comparison of Typical Physical Property Values of Liquids, Supercritical Fluids, and Gases.

| Property | Liquid | SCF | Gas |
|---|---|---|---|
| Density (g/mL) | 1 | 0.3 | $10^{-3}$ |
| Diffusivity (cm2/s) | $5 \times 10^{-6}$ | $10^{-3}$ | 0.1 |
| Viscosity (Pa · s) | $10^{-3}$ | $10^{-4}$ | $10^{-5}$ |

Likewise, "near critical" refers to the conditions at which either the temperature or pressure of at least the alcohol species or $CO_2$ gas is below but within 150K (e.g., within 50-100K), or 220 psi (e.g., within 30-150 psi) of their respective critical points. It is believed that as temperatures and pressures reach near critical, critical or supercritical conditions, the solubility of the reagents are enhanced, which promotes the esterification reaction. In other words, the $CO_2$ gas, alcohol, and acid species are better able to interact under near critical, critical or supercritical conditions than under less rigorous conditions. The reaction does not require that both the alcohol species and $CO_2$ gas be at near-critical, critical or supercritical conditions; rather, the reaction is operative as long as either one of the species satisfies such a condition.

If the present esterification reactions are operated at higher temperatures and greater pressures, up to about 250° C. or 3000 psi, respectively, and for reaction times of at least 4 hours, one can produce significant amounts of ester product at relatively greater selectivity and level of purity. At lower reaction temperatures (<190° C.), formation of monoester molecules is more prevalent, while reactions at temperatures ≥190° C. or 195° C., will convert preferentially the carboxylic acids to diesters. By selecting a temperature in a higher range from about 190° C. or 195° C. or 200° C. to about 245° C. or 250° C., one can preferentially drive the reaction to a greater rate of diester conversion. The esterification can yield a minimum of about 50%, desirably at least 65% or 70%, of a diester of the organic acid. Reactions that are performed at or near supercritical operating conditions appear to produce better results. When operated at or near critical conditions of about 250° C. for methanol and about 31° C./1000 psi for $CO_2$, one is able to achieve conversions rates of at least 90% or better, typically about 93% or 95%, for example up to about 98% or 99% conversion.

Using an amount of the alcohol solvent in excess of the carboxylic acid gas, one can produce a very clean esterification. The present synthesis process produces very clean ester products (e.g., at about 70%-72% initial purity) without generation of significant amounts of side products such as low molecular weight acids—acetic or formic acid—molecular rearrangements or cyclic products, which one could normally find in standard acid-catalyzed esterification at high temperatures. The esters can be refined to achieve about 90% to 99% purity. The purification can be accomplished, for instance, by means of crystallization, chromatography, or distillation.

As noted previously, conventional acid-catalyzed esterification requires typically about 20 hours to generate di-ester molecules. Further purification of the resulting ester requires washing with base to remove residual acid catalyst that may affect the quality of the FDCA esters in downstream processing. Other alternatives to esterification of FDCA require its activation as a diacyl chloride which makes the process not sustainable. In contrast, the advantages of the present approach enable manufacturers to make di-esters in comparatively short reaction periods (e.g., ≤6 or 7 hours) and in greater yields (e.g., ~55-90%) without the use of strong mineral acids, which can eliminate the associated purification steps.

Moreover, unlike other approaches, the process described herein is a more environmentally benign way of producing esters. As it is believed that the carbon dioxide can self-generate an acid catalyst in situ in the presence of the alcohol during the esterification reaction, the present process does not require the use or addition of another acid catalyst species. In other words, the reaction kinetics with $CO_2$ alone can drive the esterification in the substantial absence of any other acid catalyst. Hence, the process does not require activation of the FDCA as acyl chloride, which is another savings in costs and process conversion.

Section II—Examples

The following examples demonstrate the production of esters from furan dicarboxylate and an alcohol under $CO_2$ atmosphere without any other acid catalyst performed at super critical, critical, or near critical conditions for the alcohol and/or $CO_2$.

Table 1 presents some esterification reactions according to embodiments of the present method, under the reaction conditions listed therein. FDCA is reacted with an alcohol and $CO_2$: methanol is used in examples 1-3, ethanol in examples 4-6, propanol in examples 7 and 8, and 1-butanol in examples 9 and 10. In general, all of the reactions had good yields of the corresponding diester. A higher temperature, a greater pressure, and a longer reaction time, tends to give rise to a better yield. Shorter or lower alcohols species tend to produce a better yield of the corresponding diester than longer or higher alcohol solvents.

TABLE 1

| Ex. | Substrate | Alcohol | Reaction Time (h.) | Temperature (° C.) | Initial Pressure (psi) | % Yield Diester |
|---|---|---|---|---|---|---|
| 1 | Furan dicarboxylic acid (FDCA) | Methanol | 5 | 180 | 400 | 86.4 |
| 2 | FDCA | Methanol | 6 | 200 | 600 | 98.3 |
| 3 | FDCA | Methanol | 7 | 220 | 400 | 95.1 |
| 4 | FDCA | Ethanol | 5 | 190 | 400 | 85.2 |
| 5 | FDCA | Ethanol | 6 | 210 | 500 | 89.6 |
| 6 | FDCA | Ethanol | 7 | 170 | 400 | 70.0 |
| 7 | FDCA | Propanol | 5 | 200 | 500 | 80.2 |
| 8 | FDCA | Propanol | 6 | 190 | 600 | 83.1 |
| 9 | FDCA | 1-Butanol | 5 | 180 | 400 | 62.7 |
| 10 | FDCA | 1-Butanol | 6 | 200 | 500 | 77.2 |

Figure 4:
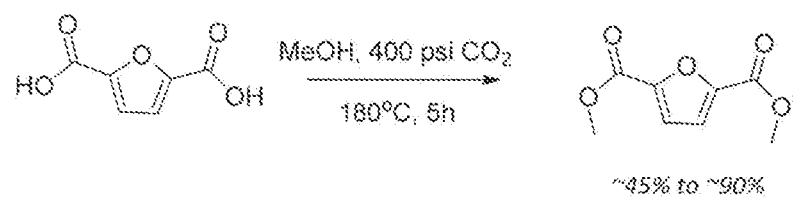
FIG. 4 is shows an esterification reaction of FDCA with methanol according to an example of the present method.

FIG. 4, is an equation of a $CO_2$-assisted esterification of FDCA with methanol, such as example 1 of Table 1. The diester yield was good at about 45%-90%, indicating that this new protocol is feasible for esterification and can lead to greater practical manipulation of FDCA. Table 1 suggests that, along with dimethylesters, esterification reactions can be optimized to convert furan dicarboxylic acid to its corresponding diester species of larger alcohols (e.g., di-ethyl, di-propyl, di-butyl esters in relatively high yield (e.g., ~60-90%) according to the present method.

The following examples are generated by reacting with methanol and ethanol as solvent but other alcohols, such as propanol or butanol, also react in a similar manner.

1. Synthesis of Mono- and Dimethyl Furan Dicarboxylate Mixture

Example 1

A 1 L autoclave reactor containing 2,5 Furan dicarboxylic acid (5 g) methanol (300 mL) was purged with $N_2$ gas and then pressurized initially with 400 psig of $CO_2$ gas. The reaction mixture was heated to 180° C. and maintained at this temperature for 5 hours. During this time the reaction pressure inside the reactor increased from 400 psig to 1600 psig. After 5 hours at 180° C., the reactor vessel was cooled to ambient room temperature and depressurized. The contents of the reactor were filtered, dried overnight under vacuum. Samples of the solid material and the solution were analyzed quantitatively for conversion using gas chromatography/mass spectrometry (GC/MS). The reaction mixture contained dimethyl ester (~23.4 wt. %), monomethyl ester (~50.6 wt. %), and unreacted FDCA (~32.8 wt. %).

Example 2

A 12 mL SS316 reactor was charged with 0.5 g of FDCA and 5 mL of methanol, along with a few crystals of dry ice ($CO_2$), which sublimates. The reactor was closed and heated to 180° C. for 4 hours in a sand bath. The internal reaction pressure was between about 1300 psig and 1700 psig. After 4 hours the reactor was cooled. The contents were filtered, dried overnight, and analyzed for dimethyl ester and other reaction intermediates. The reaction mixture included dimethyl ester (~49.8 wt. %), monomethyl ester (~35.5 wt. %), and unreacted FDCA (~14.8 wt. %). In a second reaction repeated under the same parameters, the reaction mixture contained dimethyl ester (~51.7 wt. %), monomethyl ester (~31.9 wt. %), and unreacted FDCA (~12.4 wt. %).

Example 3

Like in Example 2, a 12 mL SS316 reactor was charged with 0.5 g of FDCA and 5 mL of methanol. The reactor was closed, purged with $N_2$ gas and then pressurized initially to 400 psig with $CO_2$, and heated to 190° C. for 4 hours in a sand bath. The internal reaction pressure was between about 1400 psig and 1800 psig. After 4 hours the reactor was cooled. The contents were filtered, dried, and analyzed for dimethyl ester and other reaction intermediates. The reaction mixture included dimethyl ester (~62.3 wt. %), monomethyl ester (~31.6 wt. %), and unreacted FDCA (~6.7 wt. %).

Example 4

A 12 mL SS316 reactor was charged with 0.5 g of FDCA and 5 mL of methanol. A few crystals of dry ice were added to reactor and the reactor was closed and heated to 200° C. for 4 hours in a sand bath. The internal reaction pressure was between about 1600 psig and 1900 psig. After 2 hours the reactor was cooled. The contents were filtered, dried overnight, and analyzed using GS/MC. The reaction mixture included dimethyl ester (~70.3 wt. %), monomethyl ester (~29.1 wt. %), and unreacted FDCA (~2.4 wt. %).

Example 5

In a repeat of Example 4, a 12 mL SS316 reactor was charged with 0.5 g of FDCA and 5 mL of methanol. A few crystals of dry ice were added to reactor and the reactor was heated to 200° C. for 4 hours in a sand bath. The internal reaction pressure was between about 1500 psig and 2000 psig. After 4 hours the reactor was cooled. The contents were filtered, dried overnight, and analyzed. The reaction mixture contained dimethyl ester (~81.3 wt. %), monomethyl ester (~24.56 wt. %), and unreacted FDCA (~0.92 wt. %).

Example 6

A 12 mL SS316 reactor was charged with 0.5 g of FDCA and 5 mL of methanol. A few crystals of dry ice were added to the reactor and reactor was closed and heated to 200° C. for 6 hours in a sand bath. The internal reaction pressure was between about 1200 psig and 1800 psig. After 6 hours the reactor was cooled. The contents were filtered, dried overnight, and analyzed. The reaction mixture included dimethyl ester (~89.2 wt. %), monomethyl ester (~10.3 wt. %), and unreacted FDCA (~0.67 wt. %).

2. Synthesis of Mono- and Diethyl Furan Dicarboxylate

Example 7

Charging a 1 liter (L) autoclave reactor with 5 g. of 2,5-furan dicarboxylic acid and 300 mL of ethanol, the reactor was pressurized initially with 400 psig of $CO_2$. The reaction mixture was heated to about 180° C. and maintained at this temperature for 4 hours. During this timer the pressure inside the reactor increase from 400 psig to about 1600 psig. After 4 hours at 180° C., the reactor was cooled to ambient room temperature and depressurized. The contents of the reactor were filtered, dried overnight under vacuum, and analyzed for conversion using GC/MS. The reaction mixture contained diethyl ester (~22.7 wt. %), monoethyl ester (~51.6 wt. %) and unreacted FDCA (~25.8 wt. %).

Example 8

A 12 mL stainless steel reactor was charged with 0.5 g. of FDCA and 5 mL of ethanol, along with several medium-sized crystals of dry ice. The reactor was closed and heated to 190° C. for 5 hours in a sand bath. The internal reaction pressure was between about 1100 psig and 1700 psig. After 5 hours the reactor was cooled. The contents were dried under vacuum and analyzed using GC/MS for dimethyl FDCA and other intermediates. The reaction mixture contained diethyl ester (~54.8 wt. %), monoethyl ester (~27.5 wt. %), and unreacted FDCA (~17.8 wt. %). In a second reaction repeated under the same parameters, the reaction mixture contained dimethyl ester (~55.6 wt. %), monoethyl ester (~29.2 wt. %), and unreacted FDCA (~15.3 wt. %).

Example 9

Using a 12 mL stainless steel reactor charged with 0.5 g of FDCA, 5 mL of ethanol, and an excess of dry ice crystals. The reactor is closed and heated to 200° C. for 4 hours in a sand bath. The internal reaction pressure was between about 1400 psig and 1800 psig. After 4 hours the reactor is cooled, the reaction mixture extracted, dried overnight and analyzed using GS/MS. The reaction mixture contained diethyl ester (~63.9%), monomethyl ester (~31.7%), and unreacted FDCA (~4.6%). In a second reaction repeated under the same parameters, the reaction mixture contained diethyl ester (~69.3%), monoethyl ester (~28.3%), and unreacted FDCA (~2.5%).

Example 10

Like in Example 9, a 12 mL stainless steel reactor was charged with 0.5 g of FDCA, 5 mL of ethanol, and an excess of dry ice crystals. The reactor is closed and heated to 210° C. for 5 hours in a sand bath. The internal reaction pressure was between about 1600 psig and 2200 psig. After 5 hours the reactor is cooled. The contents were dried and analyzed as above. The reaction mixture contained diethyl ester (~82.1%), monoethyl ester (~15.6%), and unreacted FDCA (~2.4%).

3. Purification of Dimethyl Furan Dicarboxylate

To purify the ester, the crude reaction mixture was re-suspended in ethyl acetate and washed with sodium bicarbonate. The unreacted FDCA and monoethyl esters were removed by washing. The ethyl acetate layer was concentrated to give the dimethyl ester. Similarly, the unreacted FDCA and monoethyl esters were removed by washing and the ethyl acetate layer was concentrated to produce the diethyl ester. Other cost effective separation and purification techniques may include crystallization.

The present invention has been described in general and in detail by way of examples. Persons of skill in the art understand that the invention is not limited necessarily to the embodiments specifically disclosed, but that modifications and variations may be made without departing from the scope of the invention as defined by the following claims or their equivalents, including other equivalent components presently known, or to be developed, which may be used within the scope of the present invention. Therefore, unless changes otherwise depart from the scope of the invention, the changes should be construed as being included herein.

We claim:

1. A method of processing furan dicarboxylic acid (FDCA), the method comprises: reacting FDCA with a first alcohol in $CO_2$ atmosphere in the substantial absence of any other catalyst to produce a first ester mixture; reacting said first ester mixture with a second alcohol in a transesterification reaction to produce a second ester mixture.

2. The method according to claim 1, wherein further comprises regenerating said first alcohol, and recycling said first alcohol back to react with additional FDCA.

3. The method according to claim 1, wherein said first alcohol is a $C_1$ to $C_{20}$ alcohol.

4. The method according to claim 1, wherein said second alcohol is a $C_2$-$C_{12}$ alcohol.

5. The method according to claim 1, wherein said first ester mixture includes either mono-esters or diesters of any one of the following species: methyl furan dicarboxylate, ethyl furan dicarboxylate, or propyl furan dicarboxylate.

6. The method according to claim 1, wherein said reaction of FDCA with an alcohol in $CO_2$ is performed under operational conditions either at supercritical, critical or near-critical reaction temperatures and pressures for said alcohol or $CO_2$.

7. The method according to claim 1, wherein said reaction of FDCA with an alcohol in $CO_2$ is performed at a reaction temperature of between about 150° C. and 250° C., at a reaction pressure of about 400 psi up to about 3000 psi.

8. The method according to claim 7, wherein said reaction of FDCA with an alcohol in $CO_2$ is performed at a reaction temperature between about 170° C. and about 230° C., at a reaction pressure of about 920 psi to about 2500 psi.

9. The method according to claim 1, wherein said first ester mixture is transesterified by means of base-catalyzed or enzymatic reactions.

10. The method according to claim 1, wherein said transesterification reaction is performed at about 80° C. to about 90° C.

11. The method according to claim 1, wherein a boiling point of said second alcohol is at least 10° C. to 20° C. greater than that of said first alcohol.

12. The method according to claim 1, wherein said transesterification reaction is by means of a lipase enzymatic reaction.

13. The method according to claim 12, wherein said lipase is of *Candida antartica*.

* * * * *